Feb. 14, 1961 E. S. BOERNER Plant Pat. 2,027
CHRYSANTHEMUM PLANT
Filed May 25, 1960
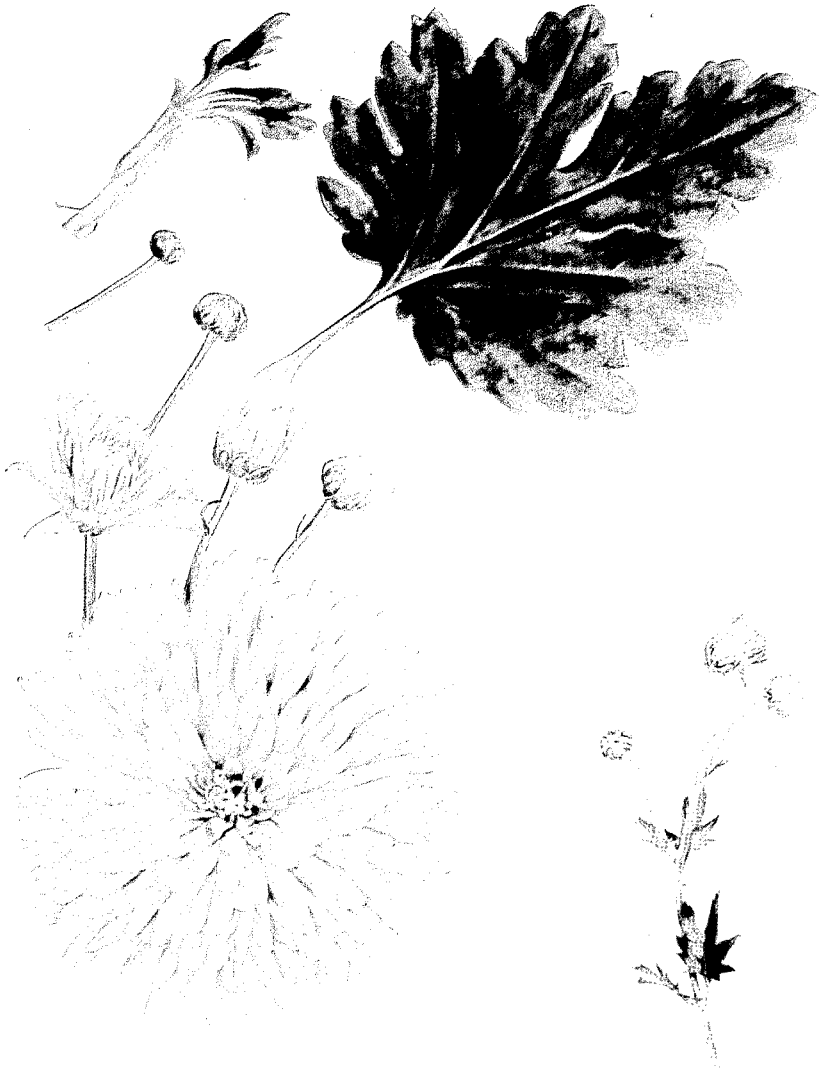
Inventor.
E. S. Boerner
By: Robb & Robb
Attorneys.

United States Patent Office

Plant Pat. 2,027
Patented Feb. 14, 1961

2,027

CHRYSANTHEMUM PLANT

Eugene S. Boerner, Newark, N.Y., assignor to Jackson & Perkins Company, Newark, N.Y., a corporation of New York Filed May 25, 1960, Ser. No. 31,789

1 Claim. (Cl. 47—60)

The present invention relates to a new and distinct variety of chrysanthemum plant of the large, rounded ball type, which was originated by me by crossing an unnamed and unpatented seedling derived from a cross of "W. F. Snyder" (unpatented) × "Mrs. Dupont" (unpatented) with the variety "Meadowlark" (Plant Patent No. 1,305).

The primary objective of this breeding was to produce a new chrysanthemum variety having the flower color and vigor of the unnamed seedling parent, combined with the earliness and vigor of the parent variety "Meadowlark." This objective was fully achieved, along with other desirable improvements, as evidenced by the following unique combination of characteristics which are outstanding in the new variety and which distinguish it from its parents, as well as from all other varieties of which I am aware:

(1) A vigorous habit of growth and airy form of the plant;

(2) An early blooming habit;

(3) Stiff flower stems;

(4) Large, rounded ball form of the flowers; and (5) A distinctive Scarlet general color tonality of the flowers.

Asexual reproduction of my new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black and white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, in the early morning during the middle of the month of October:

Parentage: Seedling.

*Seed parent.*—An unnamed seedling of "W. F. Snyder" × "Mrs. Dupont."

*Pollen parent.*—"Meadowlark."

Classification: Large, rounded ball type.

Growth: Medium tall.

Cold resistance: Very winter hardy in northern New York State.

Blooming period: In the Newark, New York climatic area, blooming usually commences about the end of September, with blooms continuing until freezing weather.

*Flower*

Bud:

*Color.*—When sepals first divide—Citron Yellow, Plate 16, lightly overcast with Carrot Red, Plate 14. When petals begin to unfurl—Jasper Red, Plate 13, lightly overcast with Eugenia Red, Plate 13. When half-blown:—inside of petals—Scarlet-Red, Plate 1, lightly overcast with Scarlet, Plate 1; outside of petals—Salmon-Orange, Plate 2, lightly overcast with Scarlet, Plate 1.

*Peduncle.* — Color — Absinthe Green, Plate 31. Strength—strong.

Bloom:

*Size.*—4½ inches.

*Stem.*—Extra strong; stiff.

*Form.*—Large, rounded ball type.

*Color.*—Center of flower—Scarlet, Plate 1, lightly overcast with Scarlet-Red, Plate 1. Outer petals—Peach Red, Plate 1, lightly overcast with Scarlet, Plate 1. Base of petals—Maize Yellow, Plate 4. Inside of petals—Scarlet, Plate 1. Reverse of petals—Bittersweet Pink, Plate 2.

*Petals.*—Texture—stiff. Form—oval.

*Fragrance.*—Characteristic chrysanthemum.

*Plant*

Form: Upright; airy.

Growth: Medium tall.

Foliage:

*Size.*—Medium.

*Quantity.*—Normal.

*Color.*—Upper side—Cress Green, Plate 31. Reverse side—Light Cress Green, Plate 31.

*Texture.*—Leathery.

I claim:

A new and distinct variety of chrysanthemum plant of the large, rounded ball type, substantially as herein shown and described, characterized particularly as to novelty by the unique combination of a vigorous habit of growth, airy form of the plant, an early blooming habit, stiff flower stems, large, rounded ball form of the flowers, and a distinctive Scarlet general color tonality of the flowers.

No references cited.